United States Patent [19]

Koszalka et al.

[11] Patent Number: 5,071,983
[45] Date of Patent: Dec. 10, 1991

[54] THERAPEUTIC NUCLEOSIDES

[75] Inventors: George W. Koszalka; Thomas A. Krenitsky, both of Chapel Hill, N.C.

[73] Assignee: Burroughs Wellcome Co., Research Triangle Park, N.C.

[21] Appl. No.: 418,368

[22] Filed: Oct. 6, 1989

[51] Int. Cl.$^5$ .......................................... C07D 405/04
[52] U.S. Cl. .................................... 544/317
[58] Field of Search ........................ 514/274; 544/317

[56] References Cited

FOREIGN PATENT DOCUMENTS 0216511  4/1987  European Pat. Off. .
0206497 12/1988  European Pat. Off. .
88/07532  3/1988  PCT Int'l Appl. .
88/00424  5/1988  PCT Int'l Appl. .

OTHER PUBLICATIONS

Chong-Ho Kim, et al., J. Med Chem., 1987, 30, pp. 862–866, Potential Anti-AID Drugs. 2',3'-Dideoxycytidine Analogues.

Mitsuya, et al., Proc. Natl. Acad. Sci. U.S.A., vol. 82, pp. 7096-7100, Oct. 1985, Medical Sciences, 3'-Azido-3'-deoxythymidine (BW A509U): An antiviral agent that inhibits the infectivity and cytopathic effect of human T-lymphotropic virus type III/lymphadenopathy-associated virus in vitro.

Prisbe, et al., Synthetic Communications, 15(5), pp. 401-409, 1985, A Novel and Efficient Preparation of 2',3'-Dideoxynucleosides[1].

Primary Examiner—John M. Ford
Attorney, Agent, or Firm—Donald Brown; Lawrence A. Nielsen; Hannah O. Green

[57] ABSTRACT

This invention relates to certain derivatives of 2', 3'-dideoxycytidine and their use in medical therapy particularly in the treatment of HIV infections. Also provided are pharmaceutical formulations and processes for the manufacture of the compounds according to the invention.

4 Claims, No Drawings

THERAPEUTIC NUCLEOSIDES

The present invention relates to certain derivatives of 2',3'-dideoxycytidine and their use in therapy, particularly for the treatment of certain viral infections.

In the field of antiviral chemotherapy, few drugs exist which effectively combat the virus per se, owing to the difficulty of attacking the virus while leaving uninfected host cells unimpaired. It has now been established that certain stages in the virus life-cycle, which vary from species to species, are specified by the virus itself. These stages may prove susceptible to attack where they differ sufficiently from any corresponding host-cell function. However, owing to great similarity between viral and host functions, effective treatments have proven very difficult to identify.

One group of viruses which has recently assumed particular importance are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome is incorporated into the host cell genome, allowing it to take full advantage of the host cell's transcription/translation machinery for the purposes of replication. Once incorporated, the viral DNA is virtually indistinguishable from the host's DNA and, in this state, the virus may persist for as long as the cell lives. As it is virtually invulnerable to attack in this form, any treatment must be directed at another stage of the virus life cycle and will, of necessity, have to be continued until all virus-infected cells have died.

A species of retrovirus has been reproducibly isolated from patients with AIDS, and is named as human immunodeficiency virus (HIV). This virus was previously known as human T-cell lymphotropic virus III (HTLV III), AIDS associated retrovirus (ARV), and lymphadenopathy associated virus (LAV). This virus has been shown preferentially to infect and destroy T-cells bearing the OKT[4] surface marker and is accepted as the aetiologic agent of AIDS. The patient progressively loses this set of T-cells, upsetting the overall balance of the immune system, reducing his ability to combat other infections, and predisposing him to opportunistic infections which frequently prove fatal. Thus, the usual cause of death in AIDS victims is by opportunistic infection, such as pneumonia or virally induced cancers, and not as a direct result of HIV infection.

AIDS. The patient progressively loses this set of T-cells, upsetting the overall balance of the immune system, reducing his ability to combat other infections, and predisposing him to opportunistic infections which frequently prove fatal. Thus, the usual cause of death in AIDS victims is by opportunistic infection, such as pneumonia or virally induced cancers, and not as a direct result of HIV infection.

Recently, HIV has also been recovered from other tissue types, including B-cells expressing the T[4] marker, macrophages and non-blood associated tissue in the central nervous system. This infection of the central nervous system has been discovered in patients expressing classical AIDS symptoms and is associated with progressive demyelination, leading to wasting and such symptoms as ancephalopathy, progressive dysarthria, ataxis and disorientation. Further conditions associated with HIV infection are the asymptomatic carrier state, progressive generalised lymphadenopathy (PGL), peripheral neuropathy and AIDS-related complex (ARC).

2',3'-Dideoxycytidine (DDC) is a compound known for its potent anti-HIV activity. The compound and its preparation are disclosed in EP Patent Specification 0216511.

Esters of the parent compound DDC have previously been disclosed generically in EP Patent Specification 206497.

2',3'-Dideoxy-N4-pivaloylcytidine is allegedly described in Synth. Comm. (1985), 15(5), 401–409. However, the description in this citation identified by the code used therein as 2',3'-dideoxy-N4-pivaloylcytidine appears to be that of DDC.

We have now discovered that certain derivatives of DDC as described below, are useful for the treatment of viral infections, particularly retroviral infections and especially AIDS and show improved bioavailability over the parent compound i.e., DDC.

The above-mentioned derivatives of DDC according to the present invention are compounds of formula (I)

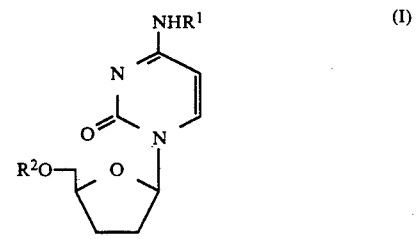

wherein $R^1$ and $R^2$ are H or alkanoyl groups containing 1-12 carbon atoms, provided that both $R^1$ and $R^2$ are not H. Preferred compounds of formula (I) are those wherein $R^1$ is not H. Preferred alkanoyl groups contain 3-5 carbon atoms. Particularly preferred alkanoyl groups are propionyl and pivaloyl.

Particularly preferred compounds according to the invention include:
1. 2',3'-dideoxy-N4,5'-O-dipropionylcytidine;
2. 2',3'-dideoxy-N4-propionylcytidine;
3. 2',3'-dideoxy-5'-O-propionylcytidine;
4. 2',3'-dideoxy-N4,5'-O-dipivaloylcytidine;
5. 2',3'-dideoxy-N4-pivaloylcytidine;
6. 2',3'-dideoxy-5'-O-pivaloylcytidine.

The advantage of the above derivatives over the parent compound DDC is their much improved bioavailability, demonstrated by the persistence of DDC in the bloodstream and the high brain levels of DDC after administration of one of the aforementioned derivatives compared with administration of DDC itself. The compounds according to the invention are therefore useful in medical therapy particularly in the treatment of HIV infections, especially those of the central nervous system.

In a further aspect of the present invention there are provided as novel compounds, the above derivatives of DDC according to the present invention with the exception of 2',3'-dideoxy-N4-pivaloylcytidine.

The compounds according to the invention are also useful for the treatment of other clinical conditions associated with retroviral infections, for example, Kaposi's sarcoma, thrombocytopenic purpura, AIDS-related complex, and patients carrying AIDS-antibodies or are seropositive to the AIDS virus as well as chronic neurological conditions such as multiple sclerosis or tropical spastic paraparesis. The compounds according to the invention are also useful for the treatment of HTLV-II, and HTLV-IV (HIV-2) infections as well as other human retrovirus infections associated with AIDS or immunodeficiency. The invention accordingly provides the compounds according to the invention for use in the treatment of any of the above infections or conditions.

According to a feature of the present invention, there is provided a method of supplying DDC to a mammal, such as a human, by administering a compound of formula (I).

Particularly good activity has been observed against those viruses which are retroviruses and also those DNA viruses with reverse transcriptase activity. Thus, there is further provided the compounds according to the invention for use in the treatment of retroviral, or retrovirus-like infections.

It will be appreciated that the compounds according to the invention may also be used in the manufacture of a medicament for the treatment of any of the above-mentioned infections or conditions.

By "a pharmaceutically acceptable derivative" is meant any pharmaceutically acceptable salt.

Any reference to any of the above compounds also includes a reference to a pharmaceutically acceptable salt thereof.

Examples of pharmaceutically acceptable salts of the compounds according to the invention and pharmaceutically acceptable derivatives thereof include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl). Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NX_4^+$ (wherein X is a $C_{1-4}$ alkyl group).

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 $\mu M$, preferably about 2 to 50 $\mu M$, most preferably about 3 to about 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present as a pharmaceutical formulation. The formulations of the present invention comprise at least one active ingredient, as above defined, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous for purine nucleoside derivatives as such compounds are susceptible to acid hydrolysis.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The above compounds according to the invention and their pharmaceutically acceptable derivatives may be employed in combination with other therapeutic agents for the treatment or prophylaxis of the above infections or conditions. Examples of such further therapeutic agents include agents that are effective for the treatment or prophylaxis of HIV infections or associated conditions, such as 3'azido-3'-deoxythymidine (zidovudine), compounds that enhance or potentiate the activity of the compounds according to the invention such as acyclic nucleosides (e.g. acyclovir), interferons such as a-interferon, renal excretion inhibitors such as probenicid or nucleoside transport inhibitors such as dipyridamole, as well as immunomodulators such as interleukin II and granulocyte macrophage colony stimulating factors.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

According to a further feature of the present invention we provide a process for the preparation of a compound according to the invention which comprises:

A) acylating 2',3'-dideoxycytidine (DDC) to effect the introduction of appropriate acyl groups at the N4- and/or 5'O-positions of DDC;

B) treating a N4, 5'-O acyl derivative according to the present invention to effect the removal of the acyl group from one of the N4- and/or 5'O-positions.

In process A) above, the acylation may be effected by the use of, for example, the appropriate acid anhydride or similar acylating agent, preferably under basic conditions e.g. in the presence of a tertiary amine such as pyridine, conveniently in a solvent medium such as acetonitrile.

In process B) above, the N4-acyl group may be selectively removed, for example by treatment with a metal halide such as zinc bromide conveniently in a solvent medium such as methanol. Selective removal of the 5'-acyl group may be effected for example by treatment with an esterase enzyme, for example porcine liver esterase type 1.

EXAMPLE 1:

2',3'-Dideoxy-$N^4$, 5'-O-dipropionylcytidine

2',3'-Dideoxycytidine (2.4 mmoles, 0.5 g, Pharmacia, Piscataway, N.J.), dimethylaminopyridine (0.178 mmoles, 21.7 mg) triethylamine (6.34 mmoles), and propionic anhydride (5.67 mmoles; Aldrich Chemicals Milwaukee, Wis.) were suspended in 50 ml of acetonitrile. The reaction was allowed to proceed at room temperature for 24 hours after which time 10 ml of methanol were added. The solvent from the reaction was removed under vacuum and the residue chromatographed on a column of silica gel, 5×40 cm. The mobile phase was chloroform/methanol (9:1; v/v). The product containing peak was collected and the solvent removed under vacuum. The residue was dissolved in 95% ethanol/water (v/v) and dried under vacuum. This was repeated a second time. A third cycle was also initiated with the solution being filtered through a 0.45 mµ filter before drying. The residue was dissolved with water and lyophilized to yield 0.747 g of 2',3'-dideoxy-$N^4$,5'-O-dipropionylcytidine.

Anal. Calcd. for $C_{15}H_{21}N_3O_5$: Calcd: C,55.72; H,6.55; N,13.00. Found: C,55.69; H,6.56; N,12.93.

NMR and mass spectrometry were consistent with the structure.

EXAMPLE 2:

2',3'-Dideoxy-$N^4$-propionylcytidine

2',3'-Dideoxycytidine (2.4 mmoles, 0.5 g, Pharmacia, Piscataway, N.J.), dimethylaminopyridine (0.178 mmoles, 21.7 mg), triethylamine (6.34 mmoles, 0.886 ml) and propionic anhydride (1 ml, Aldrich Chemicals, Milwaukee, Wis.) were suspended in 50 ml of acetonitrile. The reaction was allowed to proceed at room temperature for 24 hours after which time 10 ml of methanol were added. The solvent from the reaction was removed under vacuum and the residue chromatographed on a column of silica gel, 5×40 cm. The mobile phase was chloroform/methanol (9:1; v/v). The product containing fractions were combined and the solvent removed under vacuum. The residue was dissolved with water and 320 units of porcine liver esterase type 1 (EC 3.1.1.1, Sigma Chemicals, St. Louis, Mo.) added. After 24 hours at room temperature the pH was adjusted to 7.0 from 5.5 and an additional 320 units of esterase added. One day later the reaction was complete and the solvent removed under vacuum. The residue was chromatographed on a silica gel column (5×40 cm) and eluted with chloroform/methanol (9:1, v/v). Product containing fractions were combined and the solvent removed in vacuo yielding 0.408 g of 2',3'-dideoxy-$N^4$-pivaloylcytidine that contained 0.5 equivalents of water.

Anal. Calcd. for $C_{12}H_{17}N_3O_4$ 0.5 $H_2O$: Calcd.: C,52.17; H,6.57; M,15.21. Found: C,52.25; H,6.41; N,15.11.

NMR and mass spectrometry were consistent with the structure.

EXAMPLE 3:

2′,3′-Dideoxy-5′-O-propionylcytidine

Four hundred and three milligrams from Example 1 and 1 mmole of zinc bromide in 1 ml of methanol were combined with 9 ml of chloroform/methanol (8:2, v/v) and stirred overnight at room temperature. The solvent was removed under reduced pressure and the residue chromatographed on a column containing silica gel (5×35 cm) with chloroform/methanol (8:2, v/v). Product containing fractions were combined and after the solvent was removed in vacuo, the residue was dissolved in 30% n-propanol/water (v/v). This was chromatographed on a column containing BioRad P-2 resin (5×90 cm). Product containing fractions were combined and the solvent removed under reduced pressure yielding 0.051 g of 2′,3′-dideoxy-5′-O-propionylcytidine that contained 0.25 equivalents of n-propanol.

Anal. Calcd. for $C_{12}H_{27}N_3O_4$ 0.25 $C_3H_8O$: Calcd: C,54.25; H,6.78; N,14.88. Found: C,54.41; H,6.59; N,14.83.

NMR and mass spectrometry were consistent with the structure.

EXAMPLES 4 & 5:

2′,3′-Dideoxy-$N^4$,5′-O-dipivaloylcytidine and 2′,3′-Dideoxy-$N^4$-pivaloylcytidine 2′,3′-Dideoxycytidine (2.4 mmoles, 0.5 g, Pharmacia, Piscataway, N.J.), dimethylaminopyridine (0.178 mmoles, 21.7 mg), triethylamine (6.34 mmoles), and trimethylacetic anhydride (5.67 mmoles) were suspended in 50 ml of acetonitrile. The reaction was allowed to proceed at room temperature for 48 hours after which time 10 ml of methanol was added. The solvent from the reaction was removed under vacuum and the residue chromatographed on a column of silica gel 5×40 cm. The mobile phase was chloroform/methanol (9:1; v/v). The first two UV absorbing peaks were collected separately and the solvent removed under vacuum (Peaks 1 & 2). The residue from peak 1 was dissolved in 95% ethanol/water and dried under vacuum. This was repeated a second time. A third cycle was also initiated with the solution being filtered through a 0.45 μm filter before drying. The residue was dissolved with water and lyophilization yielded 0.36 g of 2′,3′-dideoxy-$N^4$,5′-O-dipivaloylcytidine (Example 4) that analyzed containing 0.2 equivalents of water and 0.45 equivalents of ethanol.

Anal. Calcd. for $C_{19}H_{29}N_3O_5$ 0.5 $H_2O$ 0.45 $C_2H_6O$: Calcd: C,59.19; H,8.01; N,10.41. Found: C,59.34; H,7.86; N,10.24.

NMR and mass spectrometry were consistent with the structure.

Peak 2 was dissolved in 30% n-propanol/water (v/v) and chromatographed on a column containing BioRed P-2 resin (2.5×90 cm). Product containing fractions were combined and the solvent removed in vacuo to yield 0.077 g of 2′,3′-dideoxy-$N^4$-pivaloylcytidine (Example 5) that contained 0.7 equivalents of water.

Anal. Calcd. for $C_{14}H_{21}N_3O_4$ 0.7 $H_2O$; Calcd: C,54.60; H,7.33; N,13.65. Found: C,55.36; H,7.24; N,13.34.

NMR and mass spectrometry were consistent with the structure.

EXAMPLE 6:

2′,3′-Dideoxy-5′-O-pivaloylcytidine

Two hundred and ten milligrams of Example 4 and 124 mg of zinc bromide were combined with 12 ml of methanol and stirred overnight at room temperature. The solvent was then removed under reduced pressure and the residue dissolved in 30% n-propanol/water (v/v). This was chromatographed on a column containing BioRad P-2 resin (2.5×90 cm). Product containing fractions were combined and the solvent removed in vacuo yielding 0.143 g of 2′,3′-dideoxy-5′-O-pivaloylcytidine that contained 0.5 equivalents of water and 0.1 equivalents of n-propanol.

Anal. Cald. for $C_{14}H_{21}N_3O_4$ 0.5 $H_2O$ 0.1 $C_3H_8O$: Calcd: C,55.34; H,7.40; N,13.54. Found: C,55.36; H,7.24; N,13.34.

NMR and mass spectrometry were consistent with the structure.

EXAMPLE 7:

Tablet Formulations

The following formulations A and B are prepared by wet granulation of the ingredients with a solution of povidone, followed by addition of magnesium stearate and compression.

|  | mg/tablet | mg/tablet |
|---|---|---|
| Formulation A | | |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |
| Formulation C | | |
| Active ingredient | 100 | |
| Lactose | 200 | |
| Starch | 50 | |
| Povidone | 5 | |
| Magnesium stearate | 4 | |
|  | 359 | |

The following formulations, D and E, are prepared by direct compression of the admixed ingredients. The lactose in formulation E is of the direct compression type (Dairy Crest-"Zeparox").

|  | mg/tablet |
|---|---|
| Formulation D | |
| Active ingredient | 250 |
| Pregelatinised Starch NF15 | 150 |
|  | 400 |
| Formulation E | |
| Active ingredient | 250 |
| Lactose | 150 |
| Avicel | 100 |
|  | 500 |

Formulation F (Controlled Release Formulation)

The formulation is prepared by wet granulation of the ingredients (below) with a solution of povidone followed by the addition of magnesium stearate and compression.

|   |   | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P. | 28 |
| (e) | Magnesium Stearate | 7 |
|   |   | 700 |

Drug release takes place over a period of about 6–8 hours and is complete after 12 hours.

EXAMPLE 8:

Capsule Formulations

Formulation A

A capsule formulation is prepared by admixing the ingredients of Formulation D in Example 7 above and filling into a two-part hard gelatin capsule. Formulation B (infra) is prepared in a similar manner.

|   | mg/capsule |
|---|---|
| Formulation B |   |
| (a) Active ingredient | 250 |
| (b) Lactose B.P. | 143 |
| (c) Sodium Starch Glycollate | 25 |
| (d) Magnesium Stearate | 2 |
|   | 420 |
| Formulation C |   |
| (a) Active ingredient | 250 |
| (b) Macrogol 4000 B.P. | 350 |
|   | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
|   | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|   |   | mg/capsule |
|---|---|---|
| (a) | Active ingredient | 250 |
| (b) | Microcrystalline Cellulose | 125 |
| (c) | Lactose B.P. | 125 |

-continued

|   |   | mg/capsule |
|---|---|---|
| (d) | Ethyl Cellulose | 13 |
|   |   | 513 |

EXAMPLE 9:

Injectable Formulation

| Formulation A |   |
|---|---|
| Active ingredient | 0.200 g |
| Hydrochloric acid solution, 0.1 M q.s. to pH | 4.0 to 7.0 |
| Sodium hydroxide solution, 0.1 M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B |   |
|---|---|
| Active ingredient | 0.125 g |
| Sterile, pyrogen-free, pH 7 phosphate buffer, q.s. to | 25 ml |

EXAMPLE 10:

Intramuscular Injection

| Active ingredient | 0.20 g |
|---|---|
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 11:

Syrup

| Active ingredient | 0.2500 g |
|---|---|
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water q.s. to | 5.0000 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 12:

Suppository

|  | mg/suppository |
|---|---|
| Active ingredient (63 μm)* | 250 |
| Hard Fat, BP (Witepsol H15 - Dynamit NoBel) | 1770 |
|  | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 13:

Pessaries

|  | mg/pessary |
|---|---|
| Active ingredient (63 μm) | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

Antiviral Activity

The compounds of Examples 1-6 were tested for activity against HIV generally in accordance with the method described by Mitsuya et al, Proc. Nat. Acad. Sci, USA Vol 82, pp 7096-7100, October 1985 and found to have activity against HIV at the following concentrations:

| Example | % Protection | Concentrations (μM) |
|---|---|---|
| Ex 1 | — | 25 |
| Ex 4 | — | 25 |
| Ex 5 | 42% | 100 |
| Ex 6 | 88% | 6.4 |
| DDC | 99% | 16 |

| Example | IC$_{50}$ μm |
|---|---|
| Ex 2 | 36 |
| Ex 3 | 1.6 |

Disposition of 2',3'-Dideoxycytidine and Its Congeners After Oral Dosing of Rats Using an intragastric needle, sexually mature, male Sprague Dawley rats were given single 25 mg/kg oral doses of DDC or equimolar doses of DDC Congeners.

For urinary and fecal excretion studies, each compound was administered to two animals, which were housed separately in metabolic cages and urine and feces were separated and collected during the 0-24, 24-48 and 48-72 hour intervals post dose. To prevent bacterial growth, sodium azide was placed in the urine collection vessel so that the final concentration, after 24 hours of urine collection, would be about 0.02%. Feces were weighed, homogenized in 9 volumes (9 ml/g) deionized water and centrifuged (12,000×g, 4° C., 30 min). Prior to high-performance liquid chromatographic (HPLC) analysis for drug and metabolite content, samples of the fecal homogenate supernatants and urines were filtered (0.22 μm filters).

For concomitant plasma and brain level studies, each compound was administered to two animals. Animals were sacrificed by decapitation, one of each pair at 30 minutes and the other at 2 hours post dose. Blood was collected into heparinized cups and plasma was prepared. Samples of each plasma were ultrafiltered (Amicon Centrifree Micropartition Systems) prior to HPLC analysis. Brains were removed, weighed, homogenized in 2 volumes (2 ml/g) deionized water and centrifuged (12,000×g 4° C., 30 min). The resulting supernatants were filtered (0.22 μm filters) prior to HPLC analysis.

A dual-pump HPLC system was used to analyse samples of urine, feces, plasma and brain for DDC and its congeners and their metabolites. The solvent for pump A was 25 mM phosphoric acid, buffered to pH 7.2 with ammonium hydroxide. The solvent for pump B was 60% acetonitrile in solvent A. Samples were injected onto an Adsorbospher phenyl column (4.6×250 mm, 5 micron spherical packing) and eluted at a flow rate of 1 ml/minute using linear increases in solvent B from 0 to 15% over 15 minutes and from 15 to 100% over 21 minutes, with 5 minute purge (100% B) and 15 minute restore (0% B) period between injections. The absorbance of the column effluent was monitored at 273 and 254 nm. Concentrations of compounds were determined by comparing appropriate peak areas to standard curves obtained from analysis of aqueous solutions of authentic standards. Compounds were identified by comparing retention times and ratios of peak areas at 273 and 254 nm to those of authentic standards.

RESULTS

After DDC (25 mg/kg) was administered orally to two rats, limited gastrointestinal absorption was observed. An average of 43.0% of the dose was excreted in the urine in 72 hours as unchanged drug. Fecal excretion of parent compound and 2',3'-dideoxyuridine accounted for an average of 28.1 and 1.9% of the dose, respectively. No other metabolites could be identified.

After oral administration of the compound of Example 6, the dose was completely recovered in the urine as DDC (average recovery was 105.1% of dose), indicating complete absorption and hydrolysis of the dosed compound. No Example 6 compound was excreted in the urine. In addition, no Example 6 compound, DDC or 2',3'-dideoxyuridine could be detected in the feces.

Rats dosed with the compound of Example 4 excreted an average of 23.0% of the dose in the urine as DDC and 58.3% as Example 5 compound. Thus, 81.3% of the dose was accounted for. No unchanged compound of Example 4 was excreted in the urine and no Example 4 compound, Example 5 compound, DDC or 2',3'-dideoxyuridine could be detected in the feces.

Comparable results were obtained after rats were given an oral dose of the compound of Example 1. The mean urinary excretion of DDC and Example 2 compound accounted for 40.3 and 45.4% of the dose, respectively, for a total of 85.7% of dose. No parent compound was found in the urine and no Example 1 compound, Example 2 compound, DDC or 2',3'-dideoxyuridine could be detected in the feces.

The results of the metabolic disposition study suggest that, in the rat, the 5'-ester linkage is easily hydrolyzed, while the $N^4$-amide linkage is cleaved more slowly. In addition, the results suggest that the oral bioavailability of DDC is increased 2.5-fold when the compound is administered as the 5'-pivalate congener (the compound of Example 6).

The concomitant plasma and brain levels of DDC and its congeners in rats 0.5 and 2 hours after intragastric intubation of doses equivalent to 25 mg DDC were determined. After a dose of Example 4 compound, Example 1 compound or Example 5 compound, plasma and brain levels of DDC were lower than what was observed after dosing with DDC. Much higher amounts of the analogues still containing the $N^4$-amide substitution were found in both plasma and brain. As compared to after a dose of DDC, doses of compounds of Example 3 or Example 6 (congeners with only 5'-ester substitutions) produced higher levels of DDC in the plasma and brain at 0.5 hour post dose. At 2 hours post dose, however, the plasma and brain concentrations of DDC were lower than those observed after a dose of DDC. In no case was any analogue containing the 5'-ester substitution detected in either plasma or brain.

The results again indicate that the 5'-ester linkage is readily hydrolyzed, while the $N^4$-amide substitution is much more metabolically stable. The congeners with the $N^4$-amide linkage do penetrate the blood-brain barrier but are apparently stable in the brain and do not generate significant levels of DDC after penetration occurs. The plasma level data suggest that the analogues with the single 5'-ester substitution are more rapidly absorbed and readily hydrolyzed to yield higher concentrations of DDC early after dosing, whereas the absorption of DDC although incomplete, may be more prolonged.

TABLE 1

Urinary and Fecal Recoveries of Oral Doses of DDC Its 5'-O-Ester and N4- Amide Congeners

| Compound Dosed | Rat | Sample | Compound Detected | Percent Dose Excreted |
|---|---|---|---|---|
| DDC | 1 | 0–24 hr Urine | DDC | 46.6 |
| | | 24–72 hr Urine | DDC | 6.23 |
| | | 0–24 hr Feces | DDC | 12 |
| | | | ddU* | 1.1 |
| | | 24–72 hr Feces | none | |
| DDC | 2 | 0–24 hr Urine | DDC | 31.6 |
| | | 24–72 hr Urine | DDC | 1.5 |
| | | 0–24 hr Urine | DDC | 32.2 |
| | | | ddU* | 2.6 |
| | | 24–72 hr Feces | none | |
| Ex 4 | 5 | 0–24 hr Urine | DDC | 20.4 |
| | | | Ex 5 | 57.3 |
| | | 24–72 hr Urine | DDC | 1 |
| | | 0–72 hr Feces | none | |
| Ex 4 | 6 | 0–24 hr Urine | DDC | 22.7 |
| | | | Ex 5 | 59.3 |
| | | 24–72 hr Urine | DDC | 1.8 |
| | | 0–72 hr Feces | none | |
| Ex 1 | 7 | 0–24 hr Urine | DDC | 33.4 |
| | | | Ex 2 | 52.5 |
| | | 24–72 hr Urine | DDC | 1.1 |
| | | | Ex 2 | 4.2 |
| | | 0–72 hr Feces | none | |
| Ex 1 | 8 | 0–24 hr Urine | DDC | 44.4 |
| | | | Ex 2 | 30.6 |
| | | 24–72 hr Urine | DDC | 1.7 |
| | | | Ex 2 | 3.5 |
| | | 0–72 hr Feces | none | |
| Ex 6 | 3 | 0–24 hr Urine | DDC | 92.3 |
| | | 24–72 hr Urine | DDC | 8.5 |
| | | 0–72 hr Feces | none | |
| Ex 6 | 4 | 0–24 hr Urine | DDC | 102.3 |
| | | 24–72 hr Urine | DDC | 7.2 |
| | | 0–72 hr Feces | none | |

*ddu = 2',3'-dideoxyuridine

We claim:
1. The compound 2',3'-Dideoxy-$N^4$,5'-O-dipropionylcytidine.
2. The compound 2',3'-Dideoxy-5'-O-propionylcytidine.
3. The compound 2',3'-Dideoxy-$N^4$,5'-O-dipropionylcytidine.
4. The compound 2',3'-Dideoxy-$N^4$-propionylcytidine.

* * * * *